United States Patent [19]

Harvey et al.

[11] Patent Number: 4,459,283

[45] Date of Patent: Jul. 10, 1984

[54] STABLE DENTIFRICE

[76] Inventors: Kenneth Harvey, 82 Manchester Rd., Wilmslow, Cheshire; Stephen T. Connors, 25 Carlton Rd., Sale, Cheshire, both of England

[21] Appl. No.: 293,425

[22] Filed: Aug. 17, 1981

[30] Foreign Application Priority Data

Aug. 19, 1980 [GB] United Kingdom ................. 8026944

[51] Int. Cl.$^3$ ............................................... A61K 7/16
[52] U.S. Cl. ........................................ 424/57; 424/49; 206/524.1; 206/524.4
[58] Field of Search .................................. 424/49–58; 206/524.1, 524.4

[56] References Cited

U.S. PATENT DOCUMENTS

| 4,036,950 | 7/1977 | Baines, et al. | 424/52 |
| 4,123,517 | 10/1978 | Baines et al. | 424/52 |
| 4,238,476 | 12/1980 | Harvey | 424/52 |
| 4,264,580 | 4/1981 | Barberio | 424/49 |
| 4,301,143 | 11/1981 | Barberio | 424/49 |

*Primary Examiner*—Shep K. Rose
*Attorney, Agent, or Firm*—Robert L. Stone; Murray M. Grill; Herbert S. Sylvester

[57] ABSTRACT

Dentifrices containing chloroform and a siliceous agent have been found to cause instability and corrosion in unlined aluminium tubes. A chloroform/siliceous agent dentifrice formulation is disclosed wherein an additive comprising a mixture of phosphate esters is used to reduce or prevent corrosion and thus provide stability.

10 Claims, No Drawings

STABLE DENTIFRICE

This invention relates to a stable dentifrice and in particular to a dentifrice containing chloroform which is stabilized for use in an unlined aluminium tube.

Chloroform has been used in dentifrices in non-toxic amounts in order to provide its unique flavour effect. However, in dentifrices containing certain siliceous agents it has been found to cause instability and corrosion of unlined aluminium tubes. A discussion of this problem in dentifrices in which the siliceous agent is a silica xerogel or silica aerogel is set forth in British Patent Specification No. 1,409,289, the disclosure of which is incorporated herein by reference. That disclosure particularly describes the corrosive action and flavour, odour and colour problems which can occur when dentifrices containing chloroform are packaged in unlined aluminium tubes.

It has now been found that instability and corrosion of unlined aluminium dentifrice tubes occurs with dentifrices containing chloroform and additional siliceous materials beyond those described in British Patent Specification No. 1,409,289.

According to the present invention a stable dentifrice comprises a dentally acceptable oral vehicle and dispersed therein from 10 to 40% by weight of a siliceous polishing agent characterised as having a pH in the range from 9 to 12 in a 20% aqueous slurry, a non-toxic amount of at least 0.2% by weight of chloroform, and from 0.05 to 5% by weight of an anionic phosphate ester mixture of monoester of the formula:

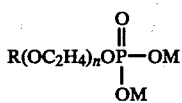

and diester of the formula:

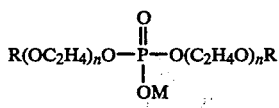

wherein R is an alkyl group of 10 to 20 carbon atoms; n is a number from 1 to 6; and M is hydrogen, alkali metal or ammonium. The ester mixture reduces or prevents corrosion and stabilises the dentifrice.

It is an advantage of this invention that a stable dentifrice containing chloroform and siliceous polishing agent is provided.

The invention also extends to such a dentifrice packed in an unlined aluminium tube.

A preferred polishing material employed in the present invention is an alkaline siliceous material characterised as having a pH in the range of 9 to 12 in a 20% aqueous slurry. Further it may contain a small amount e.g. up to about 10% or somewhat more of alumina interbonded in the silica lattice. It can be further characterised as being synthetic and amorphous and as having a refractive index between about 1.4 and 1.5. Suitable siliceous material available commercially as P.820 (Degussa), ALUSIL N (Crosfield) and ZEOLEX 24 (SiFrance). ALUSIL and ZEOLEX are trade marks. A typical material (ZEOLEX 24) is described in its manufacturer's brochure as having the following characteristics:

| Formula: $1Na_2O.1Al_2O_3.14SiO_2.nH_2O$ | | |
|---|---|---|
| SPECIFICATIONS: | | |
| Loss on ignition (900° C.) | Max % | 14 |
| pH (5 g. in 100 ml $H_2O$) | | 10.2 ± 0.2 |
| DOP (Dioctylphthalate) absorption min | ml/100 g | 180 |
| Screen Residue: | | |
| 147 microns (100 mesh) | % | 0.03 |
| 44 microns (325 mesh) | % | 1 |
| $SO_4^-$ (essentially $Na_2SO_4$) | % | 2.5 |
| AVERAGE COMPOSITION: theoretical (on dry product at 105° C.): | | |
| $SiO_2$ | % | 80.2 |
| $Al_2O_3$ | % | 9.3 |
| $Na_2O$ | % | 5.7 |
| $H_2O$ | % | 4.8 |
| PHYSICAL PROPERTIES: | | |
| Diameter of elementary particles | millimicrons | 20 to 30 |
| Surface area B.E.T. (Brunauer Emmett & Teller Method) | m/g | 160 |
| Refractive index | | 1.55 |
| Brightness, Elrepho Instrument (FMY/C Whiteness filter) | % | 98.5 |
| Absorption of liquids: | | |
| Water | ml/100 g | 160 |
| Oil | ml/100 g | 180 |
| White Spirit | ml/100 g | 370 |
| Specific gravity: | | |
| Absolute | | 2.00 |
| Tamped product (Afnor scale) | | 0.35 |
| Bagged Product | | 0.25 |

If desired, other polishing agents which as individual components do not contribute substantially to instability or corrosivity with an unlined aluminium surface may also be present. Such additional polishing agents include dicalcium phosphate dihydrate and anhydrous dicalcium phosphate as well as tricalcium phosphate calcium pyrophosphate and calcined alumina. When an additional polishing agent is present, the amount of polishing material in the dentifrice may total up to about 75% by weight, preferably 30 to 55%.

Chloroform is employed in a non-toxic amount which is effective to provide flavour to the dentifrice but which in combination with the siliceous polishing agent and in the absence of the ester mixture results in instability and corrosion in the presence of an unlined aluminium surface. Such amount can be as little as about 0.2% by weight of the dentifrice and can be even up to 8% by weight or more. An amount in the range of 0.5 to 3.5% by weight is preferred. It is noted that in view of the toxic properties of large amounts of chloroform some countries have or are establishing legal limits on the maximum amount of chloroform which can be used in products such as dentifrices, providing a safety margin by not approaching the toxic threshold too closely. However, even given such legal maxima, the effect of the present invention can be observed when non-toxic amounts such as 8%, 5%, 3.5%, 0.5% or 0.2% by weight of chloroform are present.

The anionic phosphate esters are mixtures of mono and di-esters of the formulas set forth above. Suitable esters are available from MoDo Kemi Aktiebolaget, formerly Berol Aktiebolaget, of Sweden under the name BEROL (BEROL is a trade mark) and may include an anionic triester moiety too, as well as some non-ionic portion. BEROL 729 has alkyl chain lengths of 16 to 18 carbon atoms and contains series of 4 ethylene oxide units. BEROL 729 is generally used in neutralised or partially neutralised form.

Further anionic phosphate esters which may be used in acid or neutralised forms are BEROL 525 which contains alkyl groups of 10 to 18 carbon atoms and series of 5 ethylene oxide units and BEROL 513 which also contains alkyl groups of 16 to 18 carbon atoms. However, BEROL 525, is also preferred in neutralised or partially neutralised form. Further BEROL anionic phosphate esters are available as BEROL 521, BEROL 724 and BEROL 733. The weight ratio of monoester to diester may vary, typically from about 1:10 to 10:1.

When the acid forms of the anionic phosphate ester surface active agents are neutralised or partially neutralised, alkali metal, preferably sodium, or ammonium cations are present.

Desirably the pH (20% slurry) of the completed dentifrice is in the range from 6.5 to 8, preferably 6.5 to 7.5. If appropriate, the pH may be adjusted, for instance with phosphoric acid.

The preferred anionic phosphate ester is BEROL 513.

The anionic phosphate ester is used in an amount up to about 5% by weight effective to stabilise the dentifrice in an unlined aluminium tube. This amount can be as little as about 0.05% and would depend, at least in part on the amounts of chloroform and siliceous polishing agent present. For instance with about 3.5% chloroform, it is desirable to employ about 1.5% of the anionic phosphate ester. A typical ester content would be in the range of 0.1 to 2% by weight, preferably 0.5 to 1.5%.

Besides stabilising the dentifrice the anionic phosphate ester also provides surface active properties. Such surface active properties are described in British Patent Specification Nos. 1,475,251 and 1,475,252.

The dentifrice contains a liquid vehicle which may comprise water, typically in amount of 10–90% by weight of the preparation. The liquid vehicle may additionally or alternatively comprise humectants such as glycerine, sorbitol solution or propylene glycol. A mixture of water and glycerine and/or sorbitol solution is particularly advantageous. Visually clear gels preferably contain 0 to 10% by weight of water, 0 to 80% by weight of glycerine, and 20 to 80% by weight by sorbitol. Opaque pastes preferably contain 20 to 30% by weight of humectant and 0 and to 45% by weight of water.

The solid portion of the vehicle of the dentifrice is a gelling agent or binder such as hydroxyethyl cellulose and hydroxypropyl cellulose, Irish moss, gum tragacanth, sodium carboxymethyl cellulose, polyvinyl pyrrolidone, xanthan, starch and water-soluble hydrophilic colloidal carboxyvinyl polymers such as those sold as CARBOPOL 934 and 940 (CARBOPOL is a trade mark).

The dentifrices may include an organic surface active agent in addition to the anionic phosphate ester stabilising agent. Such additional agent may be anionic, non-ionic, cationic or ampholytic in nature, and it is preferred to employ as the surface active agent a detersive material which imparts to the dentifrice detersive and foaming properties. Suitable types of such detergents are water-soluble salts of higher (i.e. having at least 12 carbon atoms) fatty acid monoglyceride monosulphates, such as the sodium salt of the monosulphated monoglyceride of hydrogenated coconut oil fatty acids, higher alkyl sulphates, such as sodium lauryl sulphate, alkyl aryl sulphonates, such as sodium dodecyl benzene sulphonate, olefin sulphonates, such as sodium olefin sulphonate in which the olefin group contains 12–21 carbon atoms, higher alkyl sulphoacetates, higher fatty acid esters of 1,2-dihydroxy propane sulphonates, and the substantially saturated higher aliphatic acyl amides of lower (i.e. having not more than 4 carbon atoms) aliphatic amino carboxylic acid compounds, such as those having 12 to 16 carbons in the fatty acid, alkyl or acyl radicals. Examples of the last mentioned amides are N-lauroyl sarcosine, and the sodium, potassium and ethanolamine salts of N-lauroyl, N-myristoyl or N-palmitoyl sarcosine, which should be substantially free from soap or similar higher fatty acid material which tends to substantially reduce the effect of these compounds. The use of these sarcosine compounds in dentifrices is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates of sorbitan monostearate with approximately 60 moles of ethylene oxide condensates of ethylene oxide with propylene glycol ("Pluronics"—PLURONIC is a Trade Mark) and amphoteric agents such as quaternised imidazole derivatives, which are available under the trade mark MIRANOL such as MIRANOL C2M. Cationic surface active germicides and anti-bacterial compounds such as diisobutylphenoxyethoxyethyl dimethyl benzyl ammonium chloride, tertiary amines having one fatty alkyl group (of from 12-18 carbon atoms) and two (poly)oxyethylene groups attached to the nitrogen (typically containing a total of from 20 to 50 ethanoxy groups per molecule) and salts thereof with acids, and compound of the structure

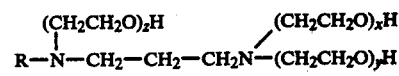

wherein R is a fatty alkyl group typically containing from 12 to 18 carbon atoms, and x, y and z total 3 or higher, as well as salts thereof with mineral or organic acids, may also be used.

The total amount of surface active agent, including the anionic phosphate ester typically does not exceed about 5%.

In certain forms of this invention a fluorine-providing compound is present in the oral preparation. These compounds may be slightly soluble in water or may be fully water-soluble. They are characterised by their ability to release fluoride ions in water and by substantial freedom from reaction with other compounds of the oral preparation. Among these materials are inorganic fluoride salts, such as suitable alkali metal, alkaline earth metal, and heavy metal salts, for example, sodium fluoride, potassium fluoride, ammonium fluoride, a copper fluoride, such as cuprous fluoride, zinc fluoride, a tin fluoride such as stannous fluoride, or stannous chlorofluoride, sodium fluorosilicate, ammonium fluorosilicate, sodium fluorozirconate, sodium monfluorophosphate, aluminium mono and di-fluorophosphate, and fluorinated sodium calcium pyrophosphate. Alkali metal and tin fluorides, such as sodium monofluorophosphate are preferred. A mixture of sodium fluoride and sodium monofluorophosphate is also highly desirable.

The amount of the fluorine-providing compound is dependent to some extent upon the type of compound, its solubility, and the type of oral preparation, but it must be a non-toxic amount. It is considered that an amount of such compound which releases a maximum of 1% by weight, based on the weight of the preparation, is satisfactory. Any suitable minimum amount of such compound may be used, but it is preferable to employ sufficient compound to release from 0.005% to 1%, most preferably about 0.1%, by weight of fluoride ion. Typically, in the cases of alkali metal fluoride and stannous fluoride, this component is present in an amount up to 2% by weight, based on the weight of the preparation, and preferably in the range of from 0.05% to 1%. In the case of sodium monofluorophosphate the compound may be present in an amount up to 7.6% by weight, more typically 0.76%.

Antibacterial agents may also be present, typically in an amount of 0.01–5% by weight. Typical antibacterial agents include $N^1$-(4-chlorobenzyl)-$N^5$-(2,4-dichlorobenzyl)biguanide;
p-chlorophenylbiguanide;
4-chlorobenzhydrylbiguanide;
4-chlorobenzhydrylguanylurea;
N-3-lauroxypropyl-$N^5$-p-chlorobenzylbiguanide;
1,6-di-p-chlorophenylbiguanidohexane; (chlorhexidine);
1,6-bis(2-ethylhexylbiguanido)hexane;
1-(lauryldimethylammonium)-8-(p-chlorobenzylidimethylammonium)octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydro pyrimidine; and their non-toxic acid addition salts.

Various other materials may be incorporated in the oral preparations of this invention. Examples are colouring or whitening agents, preservatives, silicones, chlorophyll compounds, and ammoniated material such as urea, diammonium phosphate, and mixtures thereof.

These adjuvants, where present, are incorporated in the preparations in amounts which do not substantially adversely affect the properties and characteristics desired. Whitening agents such as titanium dioxide or zinc oxide, typically in amount of 0.2 to 1% by weight provide a particularly fine cosmetic appearance to the dentifrice.

In addition to the flavour effect provided by the chloroform, the dentifrice may contain further suitable flavouring and/or sweetening materials may also be employed. Examples of suitable flavouring constituents are flavouring oils, e.g. oils of spearmint, peppermint, wintergreen, sassafras, clove, sage, eucalyptus, marjoram, cinnamon, lemon and orange, and methylsalicylate. Suitable sweetening agents include sucrose, lactose, maltoses, sorbitol, sodium cyclamate, perillartine and saccharin. Suitably flavour and sweetening agents may together comprise from 0.01% to 5% or more of the preparation.

The dentifrice is typically prepared by dispersing the polishing material and the phosphate ester in the dental vehicle and other components, except for chloroform, and then after deaeration introducing chloroform in a closed vacuum system.

The dentifrice is then placed in an unlined aluminium tube. It is noted that the term "unlined aluminium tube" refers to a tube having exposed aluminium inner surface. This can occur even where a layer over the aluminium is employed, when there are cracks in the layer.

The following Examples illustrate the present invention. All amounts and proportions are by weight unless otherwise indicated.

EXAMPLE

The following dentifrices are prepared:

| INGREDIENTS | PARTS | | | | | | |
|---|---|---|---|---|---|---|---|
| | A | B | C | D | E | F | G |
| Glycerine | 25.00 | 25.00 | — | — | — | — | — |
| Sorbitol (70%) | — | — | 25.00 | 25.00 | 25.00 | 25.00 | 25.00 |
| Sodium carboxymethyl cellulose | 1.10 | 1.10 | 1.10 | 1.10 | 1.10 | 1.20 | 1.20 |
| Titanium dioxide | 0.40 | 0.40 | 0.40 | 0.40 | 0.40 | 0.40 | 0.40 |
| Saccharic acid | 0.12 | 0.12 | — | — | — | 0.12 | 0.12 |
| Sodium saccharin | — | — | 0.18 | 0.18 | 0.18 | — | — |
| Sodium monofluorophosphate | 0.76 | 0.76 | 0.82 | 0.82 | 0.82 | 0.80 | 0.80 |
| Water | 37.05 | 39.05 | 34.95 | 33.50 | 36.50 | 36.71 | 38.21 |
| Sodium aluminosilicate(Alusil N) | 20.00 | 20.00 | 20.00 | 20.00 | 20.00 | 20.00 | 20.00 |
| Calcined alumina | 10.00 | 10.00 | 10.00 | 10.00 | 10.00 | 10.00 | 10.00 |
| Sodium lauryl sulphate | 1.77 | 1.77 | 1.50 | 1.50 | 1.50 | 1.77 | 1.77 |
| Berol 513 Phosphate ester (sodium salt) | 1.50 | — | 1.50 | 3.00 | — | 1.50 | — |
| Phosphoric acid(80–90%) | 0.50 | — | 0.50 | — | — | 0.50 | 0.50 |
| Flavour | 1.30 | 1.30 | 1.00 | 1.00 | 1.00 | — | — |
| Chloroform | 0.50 | 0.50 | 3.50 | 3.50 | 3.50 | 0.70 | 0.70 |

Dentifrices A, C, D and F age well in unlined aluminium tubes over a three month period at 43° C. whereas with dentifrices B, E and G gas formation and tube swelling is observed within 3 months at 43° C.

Other siliceous materials, such as P.820 and ZEOLEX 24 may replace ALUSIL N with corresponding results. Likewise other BEROL anionic phosphate esters may replace BEROL 513 with corresponding results.

We claim:

1. A stable opaque dentifrice comprising a dentally acceptable oral vehicle and dispersed therein from 10 to 40% by weight of a sodium aluminosilicate polishing agent characterised as having a pH in the range form 9 to 12 in a 20% aqueous slurry, calcined alumina polishing agent in amount from at least about 10% by weight up to an amount such that the total polishing agent is present in amount of up to 75% by weight, a non-toxic amount of at least 0.2% by weight of chloroform, and from 0.05 to 5% by weight of an anionic phosphate ester mixture of monoester of the formula:

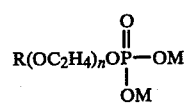

and diester of the formula:

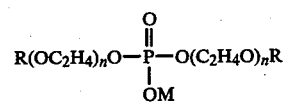

wherein R is an alkyl group of 10 to 20 carbon atoms; n is a number from 1 to 6; and M is hydrogen, alkali metal or ammonium.

2. A dentifrice as claimed in claim 1, wherein chloroform is present in an amount in the range from 0.5 to 3.5% by weight.

3. A dentifrice as claimed in claim 2, wherein about 0.5% by weight of chloroform is present.

4. A dentifrice as claimed in claim 1, wherein the R group in the anionic phosphate ester mixture contains 16 to 18 carbon atoms and the weight ratio of monoester to diester is from about 1:10 to 10:1.

5. A dentifrice as claimed in claim 1, wherein the pH of the dentifrice is adjusted with phosphoric acid.

6. A dentifrice as claimed in claim 1, wherein the dentifrice is packed in an unlined aluminium tube.

7. The dentifrice claimed in claim 1 wherein the total polishing agent is present in amount of 30–55% by weight.

8. The dentifrice claimed in claim 1 wherein 20% by weight of said siliceous polishing agent and 10% by weight of said calcined alumina are present.

9. The dentifrice claimed in claim 1 wherein said siliceous polishing agent contains up to about 10% by weight of alumina interbonded in the silica latice.

10. The dentifrice claimed in claim 8 wherein said siliceous polishing agent contains up to about 10% by weight of alumina interbonded in the silica lattice.

* * * * *